United States Patent
Merlet et al.

(10) Patent No.: US 9,894,898 B2
(45) Date of Patent: Feb. 20, 2018

(54) AGRICULTURAL COMPOSITIONS

(75) Inventors: Stéphanie Merlet, Düsseldorf (DE); Benoit Abribat, Saint Fargeau Ponthierry (FR); Anne Paulhe Massol, Portet sur Garonne (FR); Pascal Marc, Taissy (FR)

(73) Assignee: Cognis IP Management GmbH, Düsseldorf (DE)

( * ) Notice: Subject to any disclaimer, the term of this patent is extended or adjusted under 35 U.S.C. 154(b) by 316 days.

(21) Appl. No.: 13/126,238

(22) PCT Filed: Oct. 17, 2009

(86) PCT No.: PCT/EP2009/007459
§ 371 (c)(1),
(2), (4) Date: Apr. 27, 2011

(87) PCT Pub. No.: WO2007/081553
PCT Pub. Date: Jul. 19, 2007

(65) Prior Publication Data
US 2011/0201504 A1 Aug. 18, 2011

(30) Foreign Application Priority Data

Oct. 28, 2008 (EP) .................................... 08018773

(51) Int. Cl.
| | | |
|---|---|---|
| *A01N 25/30* | (2006.01) | |
| *A01P 7/04* | (2006.01) | |
| *A01P 13/02* | (2006.01) | |
| *A01P 3/00* | (2006.01) | |
| *A01N 25/04* | (2006.01) | |
| *A01N 43/40* | (2006.01) | |
| *A01N 47/36* | (2006.01) | |

(52) U.S. Cl.
CPC .............. *A01N 25/30* (2013.01); *A01N 25/04* (2013.01); *A01N 43/40* (2013.01); *A01N 47/36* (2013.01)

(58) Field of Classification Search
CPC .... A01N 47/36; A01N 43/40; A01N 2300/00; A01N 43/42; A01N 25/30; A01N 35/10; A01N 25/04
USPC ................... 504/358; 514/777, 785
See application file for complete search history.

(56) References Cited

U.S. PATENT DOCUMENTS

| | | |
|---|---|---|
| 6,291,401 B1 | 9/2001 | Dufau et al. |
| 6,432,884 B1 | 8/2002 | Lachut |
| 2004/0224850 A1 | 11/2004 | Lindner |
| 2007/0184982 A1 | 8/2007 | Long |

FOREIGN PATENT DOCUMENTS

| | | |
|---|---|---|
| FR | 2758436 | 7/1998 |
| WO | 94/24858 | 11/1994 |
| WO | WO-94/24858 | 11/1994 |
| WO | 97/12515 | 4/1997 |
| WO | WO-97/12515 | 4/1997 |
| WO | WO-99/29171 | 6/1999 |
| WO | 99/45780 | 9/1999 |
| WO | WO-99/45780 | 9/1999 |
| WO | 2004/080177 | 9/2004 |
| WO | WO-2004/080177 | 9/2004 |
| WO | WO 2004080177 A2 * | 9/2004 |
| WO | 2005/048706 | 6/2005 |
| WO | WO-2005/048706 | 6/2005 |
| WO | 2007/031251 | 3/2007 |
| WO | WO-2007/031251 | 3/2007 |
| WO | 2007/081553 | 7/2007 |
| WO | WO-2007/081553 | 7/2007 |

OTHER PUBLICATIONS

David R. Karsa, Akzo Noble Surface Chemistry AB, Design and Selection of Performance Surfactants, CRC Press, Nov. 5, 1999, pp. 2 and 21-23.*
"International Search Report in PCT/EP2009/007459, dated Jan. 28, 2011", 3 pages.
Emulsions: Preparations and Stabilization, *The Pharmaceutics and Compounding Laboratory, University of North Carolina Eshelman School of Pharmacy*, accessed from the Internet Jun. 8, 2015 at http://pharmlabs.unc.edu/labs/emulsions/hlb.htm,2 pages.
Mollet, Hans, et al., Formulation Technology: Emulsions, Suspensions, Solid Forms, *Wiley-VCH*, Translated by H.R. Payne 2001, 69-73.

* cited by examiner

Primary Examiner — Johann R Richter
Assistant Examiner — Courtney Brown
(74) Attorney, Agent, or Firm — Armstrong Teasdale LLP

(57) ABSTRACT

Suggested is the use of a mixture, comprising (a) fatty acid alkyl esters according to general formula (I) $R^1COO-R^2$ (I) in which $R^1CO$ represents an unsaturated acyl radical having 16 to 22 carbon atoms and 1, 2 or 3 double bonds, and $R^2$ represents a $C_1$-$C_4$ alkyl radical; (b) at least two non-ionic sugar or polyol surfactants, and optionally (c) polyols as an additive for agricultural compositions.

19 Claims, No Drawings

AGRICULTURAL COMPOSITIONS

FIELD OF THE INVENTION

The present invention is related to the area of agriculture and concerns a new additive and adjuvant mixture and its use for the treatment of plants and crops.

BACKGROUND OF THE INVENTION

Biocides, and in particular pesticides such as fungicides, insecticides and herbicides, are important auxiliary agents for agriculture in order to protect and to increase crops. Depending on the various and often very specific needs, a magnitude of actives exist, which show very different chemical structures and behaviours.

Pesticide products may be formulated as liquids, powders, or granules. Solvents, emulsifiers, dispersing agents and wetting agents are normally incorporated into such compositions in order to ensure that a uniform pesticide formulation has been prepared. Successful employment of any pesticide depends upon its proper formulation into a preparation that can be easily diluted with water into ready-to-use mixtures for application onto a targeted pest and/or agricultural substrate. In addition, the market requires additives—so-called "adjuvants"—providing additional benefit to the formulation by increasing the performance of the biocides in a synergistic way. Supply industry offers a wide spectrum of products, especially formulations, intending to fulfil all requirements of the end users. Of particular interest are actives or active compositions working at the same time as adjuvant and solvent, wetting agent or emulsifier.

For example, FR 2758436 A1 discloses an adjuvant composition comprising fatty acid esters, terpene derivatives and emulsifiers. Preferably said esters are obtained from sun flower oil and comprise 1 to 11 carbon atoms in the ester moiety. The emulsifiers may represent non-ionic surfactants, literally cited are ethoxylated fatty acids. U.S. Pat. No. 6,432,884 (Cognis) also refers to adjuvant compositions comprising fatty acid alkyl esters, like for example oleic acid ethyl ester, and non-ionic surfactants, like for example sorbitan esters. International patent application WO 2004/080177 A1 (Cognis) discloses adjuvant compositions comprising fatty acid alkyl esters and a mixture of hydrophilic and hydrophobic emulsifiers.

Although the products found in the market work well there is still a desire to improve their properties. Therefore, the problem underlying the present invention has been to develop new additives for agricultural compositions with the ability simultaneously to improve the penetration of biocides into the plants, to provide higher retention and better distribution of the droplets on the surface of the leaves and therefore to achieve higher adjuvant performance at a lower dosage.

DETAILED DESCRIPTION OF THE INVENTION

The present invention refers to the use of a mixture, comprising
(a) fatty acid alkyl esters according to general formula (I)

$$R^1COO—R^2 \quad (I)$$ 

in which $R^1CO$ represents an unsaturated acyl radical having 16 to 22 carbon atoms and 1, 2 or 3 double bonds, and $R^2$ represents a $C_1$-$C_4$ alkyl radical, (b) at least two non-ionic sugar or polyol surfactants, and optionally
(c) polyols
as an additive for agricultural compositions.

Surprisingly it has been observed that the additives comprising unsaturated fatty acid alkyl esters, preferably unsaturated fatty acid ethyl esters in combination with at least two non-ionic sugar or polyol surfactants meet the complex performance profile explained above.

Mixtures according to the present invention present outstanding performance as tank-mix adjuvants for pesticide formulations: they are able to increase penetration of biocides into the plants at a reduced dosage by comparison with standard tank-mix adjuvants. Also retention and distribution of the droplets on the plants are significantly improved, contributing to an optimised and versatile performance.

Fatty Acid Alkyl Esters

Fatty acid alkyl esters (component a) represent commercially available organic products which can be obtained either from the esterification of fatty acids or preferably by transesterification of suitable natural triglycerides with the respective alcohols. According to the invention it has been found critical that said esters are derived from unsaturated natural fatty acids. Therefore, preferred sources are sun-flower oil, soy oil, canola oil, rape seed oil, olive oil and the like. It is of course also possible to start from the respective unsaturated fatty acids, for example oleic acid, linolenic acid, linoleic acid, behenic acid and their technical grade mixtures. The presence of double bonds in the acyl group of the triglyceride is essential, and more particularly high content of oleic acid has been found to be the most efficient. The recommended amount of oleic chains in the triglyceride is from 60 to 90% and more preferably more than 86% b.w. A suitable method for selecting the right starting materials is to control the oleic acid content of seeds before harvest and select the fields or field areas complying with high oleic content requirements. This method has been applied to obtain the specific high oleic sunflower oil used to manufacture the corresponding fatty acid alkyl ester of this invention. Also the alkyl moiety of the esters is important. Although basically methyl, propyl and butyl esters are suitable to work in the context of the invention, ethyl esters are showing the best performance by far. Overall, ethyl esters of high oleic sunflower oil are the most preferred species.

Non-Ionic Sugar or Polyol Surfactants

It has been found essential that the emulsifiers forming component (b) supporting the defined fatty acid alkyl esters belong either to the group of non-ionic sugar surfactants or surfactants derived from polyols, in particular polyglycerol. The preferred types are alkyl polyglycosides, sorbitan esters and polyglycerol esters; these groups also encompass the respective alkoxylation products, in particular the respective adducts of ethylene oxide. Also the invention needs the presence of at least two types of these surfactants, either
    alkyl polyglucosides+sorbitol esters or
    alkyl polyglycosides+polyglycerol esters or
    sorbitol esters+polyglycerol esters The preferred combination, however, is a mixture of at least one alkyl polyglycoside and at least one—ethoxylated—sorbitan ester, in particular in ratios by weight of about 25:75 to about 75:25.

Alkyl Polyglycosides

Alkyl (or also alkenyl) polyglycosides may be derived from aldoses or ketoses containing 5 or 6 carbon atoms, preferably glucose. Accordingly, the preferred alkyl and/or alkenyl polyglycosides are alkyl or alkenyl polyglucosides.

These materials are also known generically as "alkyl polyglycosides" (APG). The alk(en)yl polyglycosides according to the invention correspond to formula (II):

$$R^3O[G]_p \quad (II)$$

wherein $R^3$ is an alkyl or alkenyl radical having from 6 to 22 carbon atoms, G is a sugar unit having 5 or 6 carbon atoms and p is a number from 1 to 10. The index p in general formula (II) indicates the degree of polymerisation (DP degree), i.e. the distribution of mono- and polyglycosides, and is a number of 1 to 10. Whereas p in a given compound must always be an integer and, above all, may assume a value of 1 to 6, the value p for a certain alkyl polyglycoside is an analytically determined calculated quantity which is mostly a broken number. Alk(en)yl polyglycosides having an average degree of polymerisation p of 1.1 to 3.0 are preferably used. Alk(en)yl polyglycosides having a degree of polymerisation below 1.7 and, more particularly,—looking at the final application—between 1.2 and 1.4 are preferred. The alkyl or alkenyl radical $R^3$ may be derived from primary alcohols containing 4 to 22 and preferably 8 to 16 carbon atoms. Typical examples are butanol, caproic alcohol, caprylic alcohol, capric alcohol, undecyl alcohol, lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and technical mixtures thereof such as are formed, for example, in the hydrogenation of technical fatty acid methyl esters or in the hydrogenation of aldehydes from Roelen's oxo synthesis. Alkyl polyglucosides based on hydrogenated $C_8$-$C_{16}$ coconut oil alcohol having a DP of 1 to 3 are preferred.

Sorbitan Esters and Ethoxylated Sorbitan Esters

Suitable sorbitan esters are sorbitan monolaurate, monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 20 moles ethylene oxide onto the sorbitan esters mentioned are also particularly efficient.

Polyglycerol Esters

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera BeBine), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylol propane or pentaerythritol with lauric acid, coco-fatty acid, tallow fatty acid, palmitic acid, stearic acid, oleic acid, behenic acid and the like optionally reacted with 1 to 30 mol ethylene oxide.

Polyols

The presence of polyols (component c) in the mixture is advantageous, since these compounds do not only serve as humectants, but also contribute to the adjuvant properties of the total composition. Examples for suitable polyols are the following:

glycerol;
alkylene glycols such as, for example, ethylene glycol, diethylene glycol, propylene glycol, butylene glycol, hexylene glycol and polyethylene glycols with an average molecular weight of 100 to 1000 Dalton;
technical oligoglycerol mixtures with a degree of self-condensation of 1.5 to 10, such as for example technical diglycerol mixtures with a diglycerol content of 40 to 50% by weight;
methylol compounds such as, in particular, trimethylol ethane, trimethylol propane, trimethylol butane, pentaerythritol and dipentaerythritol;
lower alkyl glucosides, particularly those containing 1 to 8 carbon atoms in the alkyl group, for example methyl and butyl glucoside;
sugar alcohols containing 5 to 12 carbon atoms, for example sorbitol or mannitol,
sugars containing 5 to 12 carbon atoms, for example glucose or sucrose;
amino sugars, for example glucamine;
dialcoholamines, such as diethanolamine or 2-aminopropane-1,3-diol.

The preferred polyols, however, are glucose and sorbitol.

Silicones

As an optional ingredient the compositions may also include silicones (component d), in particular as spreaders. Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates.

Additive Mixtures

In another preferred embodiment the additive mixtures according to the present invention comprise
(a) about 40% b.w. to about 70% b.w., preferably about 50% b.w. to about 60% b.w. fatty acid alkyl esters according to formula (I);
(b) about 10% b.w. to about 20% b.w., preferably about 12% b.w. to about 18% b.w. non-ionic sugar or polyglycerol surfactants; and optionally
(c) 0 to about 15% b.w., preferably about 1 b.w. to about 12% b.w. polyols; and/or
(d) 0 to about 5, preferably about 1 to about 2% b.w. silicones under the provision that the amounts add—optionally together with water—to 100% b.w. The amounts for component (b) explained above refers to the total of the at least two non-ionic surfactants. The ratio by weight between the compounds, for example between alkyl polyglycosides on one hand and sorbitan esters on the other, can be about 10:90 to about 90:10, preferably about 25:75 to about 75:25 and preferably about 40:60 to about 60:40.

INDUSTRIAL APPLICATION

Another object of the present invention is directed to an agricultural composition comprising biocides and the specific additive mixture explained above. Said biocides preferably represent herbicides, fungicides, insecticides or their mixtures. Typically the compositions comprise about 15% b.w. to about 65% b.w., preferably about 20% b.w. to about 60% b.w. and more preferably about 30% b.w. to about 50 b.w. biocides and about 35% b.w. to about 85% b.w., preferably about 40% b.w. to about 80% b.w. and more preferably about 70% b.w. to about 50 b.w. additives.

In particular, the mixture of fatty acid alkyl ester with specific non ionic surfactants described in this invention has been designed for use as a low dose or high performance tank-mix adjuvant for pesticides formulations. Said pesticides formulations preferably represent herbicides, fungicides, insecticides formulations or their mixtures. Tank-mix adjuvants and pesticides formulations are diluted in the tank by the farmers before spraying in the fields. Tank-mix adjuvants are used to improve penetration and retention of pesticides formulations and therefore optimise crop protection treatments.

Biocide Compositions

A biocide is a chemical substance capable of killing different forms of living organisms used in fields such as medicine, agriculture, forestry, and mosquito control. Usually, biocides are divided into two sub-groups:

pesticides, which includes fungicides, herbicides, insecticides, algicides, moluscicides, miticides and rodenticides, and antimicrobials, which includes germicides, antibiotics, antibacterials, antivirals, antifungals, antiprotozoals and antiparasites.

Biocides can also be added to other materials (typically liquids) to protect the material from biological infestation and growth. For example, certain types of quaternary ammonium compounds (quats) can be added to pool water or industrial water systems to act as an algicide, protecting the water from infestation and growth of algae.

Pesticides

The U.S Environmental Protection Agency (EPA) defines a pesticide as "any substance or mixture of substances intended for preventing, destroying, repelling, or mitigating any pest". A pesticide may be a chemical substance or biological agent (such as a virus or bacteria) used against pests including insects, plant pathogens, weeds, molluscs, birds, mammals, fish, nematodes (roundworms) and microbes that compete with humans for food, destroy property, spread disease or are a nuisance. In the following examples, pesticides suitable for the agrochemical compositions according to the present invention are given:

Fungicides. A fungicide is one of three main methods of pest control—the chemical control of fungi in this case. Fungicides are chemical compounds used to prevent the spread of fungi in gardens and crops. Fungicides are also used to fight fungal infections. Fungicides can either be contact or systemic. A contact fungicide kills fungi when sprayed on its surface. A systemic fungicide has to be absorbed by the fungus before the fungus dies. Examples for suitable fungicides, according to the present invention, encompass the following species: (3-ethoxypropyl)mercury bromide, 2-methoxyethylmercury chloride, 2-phenylphenol, 8-hydroxyquinoline sulfate, 8-phenylmercurioxyquinoline, acibenzolar, acylamino acid fungicides, acypetacs, aldimorph, aliphatic nitrogen fungicides, allyl alcohol, amide fungicides, ampropylfos, anilazine, anilide fungicides, antibiotic fungicides, aromatic fungicides, aureofungin, azaconazole, azithiram, azoxystrobin, barium polysulfide, benalaxy,l benalaxyl-M, benodanil, benomyl, benquinox, bentaluron, benthiavalicarb, benzalkonium chloride, benzamacril, benzamide fungicides, benzamorf, benzanilide fungicides, benzimidazole fungicides, benzimidazole precursor fungicides, benzimidazolylcarbamate fungicides, benzohydroxamic acid, benzothiazole fungicides, bethoxazin, binapacryl, biphenyl, bitertanol, bithionol, blasticidin-S, Bordeaux mixture, boscalid, bridged diphenyl fungicides, bromuconazole, bupirimate, Burgundy mixture, buthiobate, butylamine, calcium polysulfide, captafol, captan, carbamate fungicides, carbamorph, carbanilate fungicides, carbendazim, carboxin, carpropamid, carvone, Cheshunt mixture, chinomethionat, chlobenthiazone, chloraniformethan, chloranil, chlorfenazole, chlorodinitronaphthalene, chloroneb, chloropicrin, chlorothalonil, chlorquinox, chlozolinate, ciclopirox, climbazole, clotrimazole, conazole fungicides, conazole fungicides (imidazoles), conazole fungicides (triazoles), copper(II) acetate, copper(II) carbonate, basic, copper fungicides, copper hydroxide, copper naphthenate, copper oleate, copper oxychloride, copper (II) sulfate, copper sulfate, basic, copper zinc chromate, cresol, cufraneb, cuprobam, cuprous oxide, cyazofamid, cyclafuramid, cyclic dithiocarbamate fungicides, cycloheximide, cyflufenamid, cymoxanil, cypendazole, cyproconazole, cyprodinil, dazomet, DBCP, debacarb, decafentin, dehydroacetic acid, dicarboximide fungicides, dichlofluanid, dichlone, dichlorophen, dichlorophenyl, dicarboximide fungicides, dichlozoline, diclobutrazol, diclocymet, diclomezine, dicloran, diethofencarb, diethyl pyrocarbonate, difenoconazole, diflumetorim, dimethirimol, dimethomorph, dimoxystrobin, diniconazole, dinitrophenol fungicides, dinobuton, dinocap, dinocton, dinopenton, dinosulfon, dinoterbon, diphenylamine, dipyrithione, disulfiram, ditalimfos, dithianon, dithiocarbamate fungicides, DNOC, dodemorph, dodicin, dodine, DONATODINE, drazoxolon, edifenphos, epoxiconazole, etaconazole,etem, ethaboxam, ethirimol, ethoxyquin, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulf, fenapanil, fenarimol, fenbuconazole, fenfuram, fenhexamid, fenitropan, fenoxanil, fenpiclonil, fenpropidin, fenpropimorph, fentin, ferbam, ferimzone, fluazinam, fludioxonil, flumetover, flumorph, fluopicolide, fluoroimide, fluotrimazole, fluoxastrobin, fluquinconazole, flusilazole, flusulfamide, flutolanil, flutriafol, folpet, formaldehyde, fosetyl, fuberidazole, furalaxyl, furametpyr, furamide fungicides, furanilide fungicides, furcarbanil, furconazole, furconazole-cis, furfural, furmecyclox, furophanate, glyodin, griseofulvin, guazatine, halacrinate, hexachlorobenzene, hexachlorobutadiene, hexachlorophene, hexaconazole, hexylthiofos, hydrargaphen, hymexazol, imazalil, imibenconazole, imidazole fungicides, iminoctadine, inorganic fungicides, inorganic mercury fungicides, iodomethane, ipconazole, iprobenfos, iprodione, iprovalicarb, isoprothiolane, isovaledione, kasugamycin, kresoxim-methyl, lime sulphur, mancopper, mancozeb, maneb, mebenil, mecarbinzid, mepanipyrim, mepronil, mercuric chloride, mercuric oxide, mercurous chloride, mercury fungicides, metalaxyl, metalaxyl-M, metam, metazoxolon, metconazole, methasulfocarb, methfuroxam, methyl bromide, methyl isothiocyanate, methylmercury benzoate, methylmercury dicyandiamide, methylmercury pentachlorophenoxide, metiram, metominostrobin, metrafenone, metsulfovax, milneb, morpholine fungicides, myclobutanil, myclozolin, N-(ethylmercury)-p-toluenesulphonanilide, nabam, natamycin, nitrostyrene, nitrothal-isopropyl, nuarimol, OCH, octhilinone, ofurace, organomercury fungicides, organophosphorus fungicides, organotin fungicides, orysastrobin, oxadixyl, oxathiin fungicides, oxazole fungicides, oxine copper, oxpoconazole, oxycarboxin, pefurazoate, penconazole, pencycuron, pentachlorophenol, penthiopyrad, phenylmercuriurea, phenylmercury acetate, phenylmercury chloride, phenylmercury derivative of pyrocatechol, phenylmercury nitrate, phenylmercury salicylate, phenylsulfamide fungicides, phosdiphen, phthalide, phthalimide fungicides, picoxystrobin, piperalin, polycarbamate, polymeric dithiocarbamate fungicides, polyoxins, polyoxorim, polysulfide fungicides, potassium azide, potassium polysulfide, potassium thiocyanate, probenazole, prochloraz, procymidone, propamocarb, propiconazole, propineb, proquinazid, prothiocarb, prothioconazole, pyracarbolid, pyraclostrobin, pyrazole fungicides, pyrazophos, pyridine fungicides, pyridinitril, pyrifenox, pyrimethanil, pyrimidine fungicides, pyroquilon, pyroxychlor, pyroxyfur, pyrrole fungicides, quinacetol, quinazamid, quinconazole, quinoline fungicides, quinone fungicides, quinoxaline fungicides, quinoxyfen, quintozene, rabenzazole, salicylanilide, silthiofam, simeconazole, sodium azide, sodium orthophenylphenoxide, sodium pentachlorophenoxide, sodium polysulfide, spiroxamine, streptomycin, strobilurin fungicides, sulfonanilide fungicides, sulfur, sultropen, TCMTB, tebuconazole, tecloftalam, tecnazene, tecoram, tetraconazole, thiabendazole, thiadifluor, thiazole fungicides, thicyofen, thifluzamide, thiocarbamate fungicides, thiochlorfenphim, thiomersal, thiophanate, thiophanate-methyl, thiophene fungicides, thioquinox, thiram, tiadinil, tioxymid, tivedo, tolclofos-methyl, tolnaftate, tolylfluanid, tolylmercury acetate, triadimefon, triadimenol, triamiphos, triarimol, triazbutil, triazine fungicides, triazole fungicides, triazoxide, tributyltin oxide, trichlamide, tricyclazole, tridemorph, trifloxystrobin, triflumizole, triforine, triticonazole, unclassified fungicides, undecylenic acid, uniconazole, urea fungicides, validamycin, valinamide fungicides, vinclozolin, zarilamid, zinc naphthenate, zineb, ziram, zoxamide and their mixtures.

Herbicides. An herbicide is a pesticide used to kill unwanted plants. Selective herbicides kill specific targets while leaving the desired crop relatively unharmed. Some of these act by interfering with the growth of the weed and are often based on plant hormones. Herbicides used to clear waste ground are nonselective and kill all plant material with which they come into contact. Herbicides are widely used in agriculture and in landscape turf management. They are applied in total vegetation control (TVC) programs for maintenance of highways and railroads. Smaller quantities are used in forestry, pasture systems, and management of areas set aside as wildlife habitat. In the following, a number of suitable herbicides are compiled:

2,4-D, a broadleaf herbicide in the phenoxy group used in turf and in no-till field crop production. Now mainly used in a blend with other herbicides that act as synergists, it is the most widely used herbicide in the world, third most commonly used in the United States. It is an example of synthetic auxin (plant hormone).

Atrazine, a triazine herbicide used in corn and sorghum for control of broadleaf weeds and grasses. It is still used because of its low cost and because it works as a synergist when used with other herbicides, it is a photosystem II inhibitor.

Clopyralid, a broadleaf herbicide in the pyridine group, used mainly in turf, rangeland, and for control of noxious thistles. Notorious for its ability to persist in compost. It is another example of synthetic auxin.

Dicamba, a persistent broadleaf herbicide active in the soil, used on turf and field corn. It is another example of synthetic auxin.

Glyphosate, a systemic nonselective (it kills any type of plant) herbicide used in no-till burndown and for weed control in crops that are genetically modified to resist its effects. It is an example of a EPSPs inhibitor.

Imazapyr, a non-selective herbicide used for the control of a broad range of weeds including terrestrial annual and perennial grasses and broadleaved herbs, woody species, and riparian and emergent aquatic species.

Imazapic, a selective herbicide for both the pre- and post-emergent control of some annual and perennial grasses and some broadleaf weeds. Imazapic kills plants by inhibiting the production of branched chain amino acids (valine, leucine, and isoleucine), which are necessary for protein synthesis and cell growth.

Metoalachlor, a pre-emergent herbicide widely used for control of annual grasses in corn and sorghum; it has largely replaced atrazine for these uses.

Paraquat, a nonselective contact herbicide used for no-till burndown and in aerial destruction of marijuana and coca plantings. More acutely toxic to people than any other herbicide in widespread commercial use.

Picloram, a pyridine herbicide mainly used to control unwanted trees in pastures and edges of fields. It is another synthetic auxin.

Triclopyr.

Insecticides. An insecticide is a pesticide used against insects in all developmental forms. They include ovicides and larvicides used against the eggs and larvae of insects. Insecticides are used in agriculture, medicine, industry and the household. In the following, suitable insecticides are mentioned:

Chlorinated insecticides such as, for example, Camphechlor, DDT, Hexachlorocyclohexane, gamma-Hexachlorocyclohexane, Methoxychlor, Pentachlorophenol, TDE, Aldrin, Chlordane, Chlordecone, Dieldrin, Endosulfan, Endrin, Heptachlor, Mirex and their mixtures;

Organophosphorus compounds such as, for example, Acephate, Azinphos-methyl, Bensulide, Chlorethoxyfos, Chlorpyrifos, Chlorpyriphos-methyl, Diazinon, Dichlorvos (DDVP), Dicrotophos, Dimethoate, Disulfoton, Ethoprop, Fenamiphos, Fenitrothion, Fenthion, Fosthiazate, Malathion, Methamidophos, Methidathion, Methyl-parathion, Mevinphos, Naled, Omethoate, Oxydemeton-methyl, Parathion, Phorate, Phosalone, Phosmet, Phostebupirim, Pirimiphos-methyl, Profenofos, Terbufos, Tetrachlorvinphos, Tribufos, Trichlorfon and their mixture;

Carbamates such as, for example, Aldicarb, Carbofuran, Carbaryl, Methomyl, 2-(1-Methylpropyl)phenyl methylcarbamate and their mixtures;

Pyrethroids such as, for example, Allethrin, Bifenthrin, Deltamethrin, Permethrin, Resmethrin, Sumithrin, Tetramethrin, Tralomethrin, Transfluthrin and their mixtures;

Plant toxin derived compounds such as, for example, Derris (rotenone), Pyrethrum, Neem (Azadirachtin), Nicotine, Caffeine and their mixtures.

Rodenticides. Rodenticides are a category of pest control chemicals intended to kill rodents. Rodents are difficult to kill with poisons because their feeding habits reflect their place as scavengers. They would eat a small bit of something and wait, and if they do not get sick, they would continue eating. An effective rodenticide must be tasteless and odorless in lethal concentrations, and have a delayed effect. In the following, examples for suitable rodenticides are given:

Anticoagulants are defined as chronic (death occurs after 1-2 weeks post ingestion of the lethal dose, rarely sooner), single-dose (second generation) or multiple dose (first generation) cumulative rodenticides. Fatal internal bleeding is caused by lethal dose of anticoagulants such as brodifacoum, coumatetralyl or warfarin. These substances in effective doses are antivitamins K, blocking the enzymes $K_1$-2,3-epoxide-reductase (this enzyme is preferentially blocked by 4-hydroxycoumarin/4-hydroxythiacoumarin derivatives) and $K_1$-quinone-reductase (this enzyme is preferentially blocked by indandione derivatives), depriving the organism of its source of active vitamin $K_1$. This leads to a disruption of the vitamin K cycle, resulting in an inability of production of essential blood-clotting factors (mainly coagulation factors II (prothrombin), VII (proconvertin), IX (Christmas factor) and X (Stuart factor)). In addition to this specific metabolic disruption, toxic doses of 4-hydroxycoumarin/4-hydroxythiacoumarin and indandione anticoagulants are causing damage to tiny blood vessels (capillaries), increasing their permeability, causing diffuse internal bleedings (haemorrhagias). These effects are gradual; they develop in the course of days and are not accompanied by any nociceptive perceptions, such as pain or agony. In the final phase of intoxication the exhausted rodent collapses in hypovolemic circulatory shock or severe anemia and dies calmly. Rodenticidal anticoagulants are either first generation agents (4-hydroxycoumarin type: warfarin, coumatetralyl; indandione type: pindone, diphacinone, chlorophacinone), generally requiring higher concentrations (usually between 0.005 and 0.1%), consecutive intake over days in order to accumulate the lethal dose, poor active or inactive after single feeding and less toxic than second generation agents, which are derivatives of 4-hydroxycoumarin (difenacoum, brodifacoum, bromadiolone and flocoumafen) or 4-hydroxy-1-benzothiin-2-one (4-hydroxy-1-thiacoumarin, sometimes incorrectlly referred to as 4-hydroxy-1-thiocoumarin, for reason see heterocyclic compounds), namely difethialone. Second generation agents are far more toxic than first generation agents, they are generally applied in lower concentrations in baits (usually in the order of 0.001-0.005%), and are lethal after single ingestion of bait and are effective also against strains of rodents that have become resistant against first generation anticoagulants; thus the second generation anticoagulants are sometimes referred to as "superwarfarins". Sometimes, anticoagulant rodenticides are potentiated by an antibiotic, most commonly by sulfaquinoxaline. The aim of this association (e.g. warfarin 0.05%+sulfaquinoxaline 0.02%, or difenacoum 0.005%+sulfaquinoxaline 0.02% etc.) is that the antibiotic/bacteriostatic agent suppresses intestinal/gut symbiotic microflora that represents a source of vitamin K. Thus the symbiotic bacteria are killed or their metabolism is impaired and the production of vitamin K by them is diminished, an effect which logically contributes to the action of anticoagulants. Antibiotic agents other than sulfaquinoxaline may be used, for example co-trimoxazole, tetracycline, neomycin or metronidazole. A further synergism used in rodenticidal baits is that of an association of an anticoagulant with a compound with vitamin D-activity, i.e. cholecalciferol or ergocalciferol (see below). A typical formula used is, e. g., warfarin 0.025-0.05%+cholecalciferol 0.01%. In some countries there are even fixed three-component rodenticides, i.e. anticoagulant+antibiotic+vitamin D, e. g. difenacoum 0.005% +sulfaquinoxaline 0.02% +cholecalciferol 0.01%. Associations of a second-generation anticoagulant with an antibiotic and/or vitamin D are considered to be effective even against the most resistant strains of rodents, though some second generation anticoagulants (namely brodifacoum and difethialone), in bait concentrations of 0.0025-0.005% are so toxic that no known resistant strain of rodents exists and even rodents resistant against any other derivatives are reliably exterminated by application of these most toxic anticoagulants.

Vitamin $K_1$ has been suggested and successfully used as an antidote for pets or humans, which/who were either accidentally or intentionally (poison assaults on pets, suicidal attempts) exposed to anticoagulant poisons. In addition, since some of these poisons act by inhibiting liver functions and in progressed stages of poisoning, several blood-clotting factors as well as the whole volume of circulating blood lacks, a blood transfusion (optionally with the clotting factors present) can save a person's life who inadvertently takes them, which is an advantage over some older poisons.

Metal phosphides have been used as a means of killing rodents and are considered single-dose fast acting rodenticides (death occurs commonly within 1-3 days after single bait ingestion). A bait consisting of food and a phosphide (usually zinc phosphide) is left where the rodents can eat it. The acid in the digestive system of the rodent reacts with the phosphide to generate the toxic phosphine gas. This method of vermin control has possible use in places where rodents are resistant to some of the anticoagulants, particularly for control of house and field mice; zinc phosphide baits are also cheaper than most second-generation anticoagulants, so that sometimes, in cases of large infestation by rodents, their population is initially reduced by copious amounts of zinc phosphide bait applied, and the rest of the population that survived the initial fast-acting poison is then eradicated by prolonged feeding on anticoagulant bait. Inversely, the individual rodents that survived anticoagulant bait poisoning (rest population) can be eradicated by pre-baiting them with nontoxic bait for a week or two (this is important to overcome bait shyness, and to get rodents used to feeding in specific areas by offering specific food, especially when eradicating rats) and subsequently applying poisoned bait of the same sort as used for pre-baiting until all consumption of the bait ceases (usually within 2-4 days). These methods of alternating rodenticides with different modes of action provides a factual or an almost 100% eradication of the rodent population in the area if the acceptance/palatability of bait is good (i.e., rodents readily feed on it).

Phosphides are rather fast acting rat poisons, resulting in that the rats are dying usually in open areas instead of the affected buildings. Typical examples are aluminum phosphide (fumigant only), calcium phosphide (fumigant only), magnesium phosphide (fumigant only) and zinc phosphide (in baits). Zinc phosphide is typically added to rodent baits in amounts of around 0.75-2%. The baits have a strong, pungent garlic-like odor characteristic for phosphine liberated by hydrolysis. The odor attracts (or, at least, does not repulse) rodents, but has a repulsive effect on other mammals; birds, however (notably wild turkeys), are not sensitive to the smell and feed on the bait thus becoming collateral damage.

Hypercalcemia. Calciferols (vitamins D), cholecalciferol (vitamin $D_3$) and ergocalciferol (vitamin $D_2$) are used as rodenticides, which are toxic to rodents for the same reason that they are beneficial to mammals: they are affecting calcium and phosphate homeostasis in the body. Vitamins D are essential in minute quantities (few IUs per kilogram body weight daily, which is only a fraction of a milligram), and like most fat soluble vitamins they are toxic in larger doses as they readily result in the so-called hypervitaminosis, which is, simply said, poisoning by the vitamin. If the poisoning is severe enough (that is, if the dose of the toxicant is high enough), it eventually leads to death. In rodents consuming the rodenticidal bait it causes hypercalcemia by raising the calcium level, mainly by increasing calcium absorption from food, mobilising bone-matrix-fixed calcium into ionised form (mainly monohydrogencarbonate calcium cation, partially bound to plasma proteins, $[CaHCO_3]^+$), which circulates dissolved in the blood plasma, and after ingestion of a lethal dose the free calcium levels are raised sufficiently so that blood vessels, kidneys, the stomach wall and lungs are mineralised/calcificated (formation of calcificates, crystals of calcium salts/complexes in the tissues thus damaging them), leading further to heart problems (myocard is sensitive to variations of free calcium levels that are affecting both myocardial contractibility and excitation propagation between atrias and ventriculas) and bleeding (due to capillary damage) and possibly kidney failure. It is considered to be single-dose, or cumulative (depending on concentration used; the common 0.075% bait concentration is lethal to most rodents after a single intake of larger portions of the bait), sub-chronic (death occurring usually within days to one week after ingestion of the bait). Applied concentrations are 0.075% cholecalciferol and 0.1% ergocalciferol when used alone. There is an important feature of calciferols toxicology which is that they are synergistic with anticoagulant toxicants. This means that mixtures of anticoagulants and calciferols in the same bait are more toxic than the sum of toxicities of the anticoagulant and the calciferol in the bait so that a massive hypercalcemic effect can be achieved by substantially lower calciferol content in the bait and vice-versa. More pronounced anticoagulant/hemorrhagic effects are observed if calciferol is present. This synergism is mostly used in baits low in calciferol because effective concentrations of calciferols are more expensive than effective concentrations of most anticoagulants. The historically very first application of a calciferol in rodenticidal bait was, in fact, the Sorex product Sorexa® D (with a different formula than today's Sorexa® D) back in the early 1970's, containing warfarin 0.025%+ergocalciferol 0.1%. Today, Sorexa® CD contains a 0.0025% difenacoum+0.075% cholecalciferol combination. Numerous other brand products containing either calciferols 0.075-0.1% (e. g. Quintox®, containing 0.075% cholecalciferol) alone, or a combination of calciferol 0.01-0.075% with an anticoagulant are marketed.

Miticides, moluscicides and nematicides. Miticides are pesticides that kill mites. Antibiotic miticides, carbamate miticides, formamidine miticides, mite growth regulators, organochlorine, permethrin and organophosphate miticides all belong to this category. Molluscicides are pesticides used to control molluscs, such as moths, slugs and snails. These substances include metaldehyde, methiocarb and aluminium sulfate. A nematicide is a type of chemical pesticide used to kill parasitic nematodes (a phylum of worm). A nematicide is obtained from a neem tree's seed cake; which is the residue of neem seeds after oil extraction. The neem tree is known by several names in the world but was first cultivated in India since ancient times.

Antimicrobials. In the following examples, antimicrobials suitable for agrochemical compositions according to the present invention are given. Bactericidal disinfectants mostly used are those applying active chlorine (i.e., hypochlorites, chloramines, dichloroisocyanurate and trichloroisocyanurate, wet chlorine, chlorine dioxide, etc.), active oxygen (peroxides such as peracetic acid, potassium persulfate, sodium perborate, sodium percarbonate and urea perhydrate), iodine (iodpovidone (povidone-iodine, Betadine), Lugol's solution, iodine tincture, iodinated nonionic surfactants), concentrated alcohols (mainly ethanol, 1-propanol, called also n-propanol and 2-propanol, called isopropanol and mixtures thereof; further, 2-phenoxyethanol and 1- and 2-phenoxypropanols are used), phenolic substances (such as phenol (also called "carbolic acid"), cresols (called "Lysole" in combination with liquid potassium soaps), halogenated (chlorinated, brominated) phenols, such as hexachlorophene, triclosan, trichlorophenol, tribromophenol, pentachlorophenol, Dibromol and salts thereof), cationic surfactants such as some quaternary ammonium cations (such as benzalkonium chloride, cetyl trimethylammonium bromide or chloride, didecyldimethylammonium chloride, cetylpyridinium chloride, benzethonium chloride) and others, non-quarternary compounds such as chlorhexidine, glucoprotamine, octenidine dihydrochloride, etc.), strong oxidizers such as ozone and permanganate solutions;

heavy metals and their salts such as colloidal silver, silver nitrate, mercury chloride, phenylmercury salts, copper sulfate, copper oxide-chloride etc. Heavy metals and their salts are the most toxic and environmentally hazardous bactericides and, therefore, their use is strongly suppressed or forbidden; further, also properly concentrated strong acids (phosphoric, nitric, sulfuric, amidosulfuric, toluenesulfonic acids) and alcalis (sodium, potassium, calcium hydroxides) between pH<1 or >13, particularly below elevated temperatures (above 60° C.) kill bacteria.

As antiseptics (i.e., germicide agents that can be used on human or animal body, skin, mucoses, wounds and the like), few of the above mentioned disinfectants can be used under proper conditions (mainly concentration, pH, temperature and toxicity toward man/animal). Among them, important are Some properly diluted chlorine preparations (e. g. Daquin's solution, 0.5% sodium or potassium hypochlorite solution, pH-adjusted to pH 7-8, or 0.5-1% solution of sodium benzenesulfochloramide (chloramine B)), some iodine preparations such as iodopovidone in various galenics (ointments, solutions, wound plasters), in the past also Lugol's solution, peroxides as urea perhydrate solutions and pH-buffered 0.1-0.25% peracetic acid solutions, alcohols with or without antiseptic additives, used mainly for skin antisepsis, weak organic acids such as sorbic acid, benzoic acid, lactic acid and salicylic acid some phenolic compounds such as hexachlorophene, triclosan and Dibromol, and cation-active compounds such as 0.05-0.5% benzalkonium, 0.5-4% chlorhexidine, 0.1-2% octenidine solutions.

Bactericidal antibiotics kill bacteria; bacteriostatic antibiotics only slow down their growth or reproduction. Penicillin is a bactericide, as are cephalosporins. Aminoglycosidic antibiotics can act in both a bactericidic manner (by disrupting cell wall precursor leading to lysis) or bacteriostatic manner (by connecting to 30s ribosomal subunit and reducing translation fidelity leading to inaccurate protein synthesis). Other bactericidal antibiotics according to the present invention include the fluoroquinolones, nitrofurans, vancomycin, monobactams, cotrimoxazole, and metronidazole.

In a preferred embodiment of the present invention said biocides are selected from the group consisting of herbicides, fungicides, insecticides and their mixtures, more particularly said biocides are chosen from the group consisting of tebuconazole, oxyfluorfen, propanil, chlorpyrifos, PCNB, bifenthrin, novaluron, phenmedipham, deltamethrin, acetochlore, lambda-cyhalothrin and their mixtures.

Treatment of Plants and Crops

A final object of the present invention refers to a method for improving the growth and health of crops characterised in that the crops are treated with a composition comprising at least one biocide, preferably a pesticide, an insecticide, a herbicide or their mixtures, and the additive mixture described above. Preferably the compositions represent concentrated tank solutions, which are diluted by the farmer to a concentration of about 0.1 to 5% b.w. which can sprayed on the plants and crops directly.

EXAMPLES

Example 1 and Comparative Example C1

The adjuvant performance of a standard product taken from the market called "Crop Oil Concentrate" (Comparative Example C1) has been compared with a new adjuvant composition according to the present invention (Inventive Example 1). The compositions of the two products are shown in Table 1.

TABLE 1

| Compositions | | |
|---|---|---|
| Composition | 1 | C1 |
| Oleic ethyl sunflowerate | 60.0 | |
| Methyl canolate | | 95.0 |
| Disponil SMO/STO 20[1] | 17.1 | 5.0 |
| Glucopon ® 650 EC[2] | 10.0 | |
| Sorbitol | 10.0 | |
| Silicone Break-Thru S 240 | 2.0 | |
| Lactic acid | 0.1 | |
| Water | ad to 100 | |

[1]Sorbitanmono/trioleate + 20 EO, Cognis GmbH, Düsseldorf
[2]C$_8$-C$_{10}$ Alkyl polyglucoside, Cognis GmbH, Düsseldorf Field trials have been performed in combination with different pesticides compositions and several dosages. Results indicate that the performance of the new adjuvant composition equals standard adjuvant activity but at a much reduced dosage and for a half pesticide rate. The results are shown in the following Table 2:

TABLE 2

| Results of field trials | | | | |
|---|---|---|---|---|
| Pesticide formulation | Rate [L/ha] | Adjuvant | Rate [L/ha] | Efficiency [%-rel] |
| Celio[3] | 0.2 | C1 | 1.0 | 92.8 |
| | 0.1 | 1 | 1.0 | 94.3 |
| | 0.1 | 1 | 0.75 | 94.3 |
| | 0.1 | 1 | 0.5 | 94.0 |
| | 0.1 | 1 | 0.25 | 94.3 |
| Ogive[4] | 0.5 | C1 | 1.0 | 98.0 |
| | 0.25 | 1 | 1.0 | 98.0 |
| | 0.25 | 1 | 0.75 | 98.0 |
| | 0.25 | 1 | 0.5 | 97.0 |
| | 0.25 | 1 | 0.25 | 96.0 |
| Pesticide formulation | Rate [kg/ha] | Adjuvant | Rate [L/ha] | Efficiency [%-rel] |
| Atlantis[5] | 0.5 | C1 | 1.0 | 99.0 |
| | 0.25 | 1 | 1.0 | 99.0 |
| | 0.25 | 1 | 0.75 | 97.0 |
| | 0.25 | 1 | 0.5 | 95.0 |
| | 0.25 | 1 | 0.25 | 89.0 |

[3]Clodinafop-propargyl + cloquintocet-mexyl
[4]Clethodim
[5]Mesosulfuron-methyl sodium + iodosulfuron methyl

The invention claimed is:

1. An additive and adjuvant mixture for agricultural compositions comprising:
   (a) fatty acid alkyl esters according to general formula (I)

$$R^1COO—R^2 \quad (I)$$

wherein $R^1CO$ represents an unsaturated acyl radical having 16 to 22 carbon atoms and 1, 2 or 3 double bonds, and $R^2$ represents a $C_1$-$C_4$ alkyl radical,
   (b) at least two different types of surfactants selected from:
   a combination of alkyl polyglycosides and ethoxylated sorbitan esters,
   a combination of alkyl polyglycosides and polyglycerol esters, and
   a combination of ethoxylated sorbitan esters and polyglycerol esters,
   wherein the ethoxylated sorbitan esters are addition products of 5 to 20 moles of ethylene oxide onto a sorbitan ester; and
   (c) optionally polyols.

2. The mixture of claim 1, wherein said fatty acid alkyl esters are derived from sunflower oil, soy oil, canola oil or olive oil.

3. The mixture of claim 1, wherein said fatty acid alkyl esters are ethyl esters.

4. The mixture of claim 1, wherein said polyols represent glucose or sorbitol.

5. The mixture of claim 1, further comprising a silicone, wherein the mixture comprises
   (a) 40 to 70% b.w. fatty acid alkyl esters according to formula (I);
   (b) 10 to 20% b.w. the at least two different types of surfactants; and
   (c) 0 to 15% b.w. polyols; and/or
   (d) 0 to 5% b.w. silicones wherein the mixture adds optionally together with water to 100% b.w.

6. An agricultural composition comprising biocides and the mixture of claim 1.

7. The composition according to claim 6, wherein said biocides represent herbicides, fungicides, insecticides or their mixtures.

8. The composition according to claim 6, wherein the composition is used as a tank-mix adjuvant for pesticides formulations.

9. A method for improving the growth and health of plants and crops wherein the plants and crops are treated with a composition of claim 6.

10. A method of using an additive and adjuvant mixture comprising
(a) fatty acid alkyl esters according to general formula (I)

$$R^1COO\text{—}R^2 \qquad (I)$$

wherein $R^1CO$ represents an unsaturated acyl radical having 16 to 22 carbon atoms and 1, 2 or 3 double bonds, and $R^2$ represents a $C_1$-$C_4$ alkyl radical,
(b) at least two surfactants selected from:
a combination of alkyl polyglycosides and ethoxylated sorbitan esters,
a combination of alkyl polyglycosides and polyglycerol esters, and
a combination of ethoxylated sorbitan esters and polyglycerol esters,
wherein the ethoxylated sorbitan esters are addition products of 5 to 20 moles ethylene oxide onto a sorbitan ester; and
(c) optionally polyols
as an additive for agricultural compositions.

11. The method of claim 10, wherein said fatty acid alkyl esters are derived from (high oleic) sunflower oil, soy oil, canola oil or olive oil.

12. The method of claim 10, wherein said fatty acid alkyl esters are ethyl esters.

13. The method of claim 10, wherein said polyols represent glucose or sorbitol.

14. The mixture of claim 3, further comprising a silicone, wherein the mixture comprises
(a) 40 to 70% b.w. fatty acid alkyl esters according to formula (I);
(b) 10 to 20% b.w. the at least two different types of surfactants; and
(c) 0 to 15% b.w. polyols; and/or
(d) 0 to 5% b.w. silicones
wherein the mixture adds optionally together with water to 100% b.w.

15. The composition of claim 7, wherein the composition is used as a tank-mix adjuvant for pesticides formulations.

16. The mixture of claim 1, wherein the at least two different types of surfactants is a combination of alkyl polyglycosides and ethoxylated sorbitan esters.

17. The mixture of claim 1, wherein the at least two different types of surfactants is a combination of alkyl polyglycosides and ethoxylated sorbitan esters in a ratio of 25:75 to 75:25 by weight.

18. The mixture of claim 1, wherein $R^2$ is ethyl, and wherein the at least two different types of surfactants is a combination of alkyl polyglycosides and ethoxylated sorbitan esters.

19. The mixture of claim 1, wherein the fatty acid alkyl esters are obtained by transesterification of an alcohol $R_2$—OH with a natural triglyceride having 60 to 90% by weight of oleic chains.

* * * * *